(12) United States Patent
Raz (10) Patent No.: US 9,943,253 B2
(45) Date of Patent: Apr. 17, 2018

(54) SYSTEM AND METHOD FOR IMPROVED AUDIO PERCEPTION

(71) Applicant: Innovo IP, LLC, Aventura, FL (US)

(72) Inventor: Yair Raz, Aventura, FL (US)

(73) Assignee: INNOVO IP, LLC, Aventura, FL (US)

( * ) Notice: Subject to any disclaimer, the term of this patent is extended or adjusted under 35 U.S.C. 154(b) by 82 days.

(21) Appl. No.: 14/979,238

(22) Filed: Dec. 22, 2015

(65) Prior Publication Data
US 2016/0277855 A1    Sep. 22, 2016

Related U.S. Application Data

(60) Provisional application No. 62/177,631, filed on Mar. 20, 2015.

(51) Int. Cl.
| | |
|---|---|
| *H04R 25/00* | (2006.01) |
| *A61B 5/12* | (2006.01) |
| *H03G 5/16* | (2006.01) |
| *H04R 3/04* | (2006.01) |
| *H03G 5/02* | (2006.01) |
| *H04R 1/10* | (2006.01) |
| *H04R 5/04* | (2006.01) |

(52) U.S. Cl.
CPC ............ *A61B 5/123* (2013.01); *H03G 5/025* (2013.01); *H03G 5/165* (2013.01); *H04R 3/04* (2013.01); *H04R 1/1091* (2013.01); *H04R 5/04* (2013.01); *H04R 2205/041* (2013.01); *H04R 2430/01* (2013.01); *H04R 2430/03* (2013.01)

(58) Field of Classification Search
CPC ...... H03G 5/025; H03G 5/165; H04R 1/1091; H04R 3/04; H04R 5/04; H04R 2205/041; H04R 2430/01; H04R 2430/03

USPC ................. 381/98, 101, 102, 103, 312, 315
See application file for complete search history.

(56) References Cited

U.S. PATENT DOCUMENTS

| | | | |
|---|---|---|---|
| 4,284,847 | A  | 8/1981 | Besserman |
| 6,118,814 | A  | 9/2000 | Friedman |
| 6,799,164 | B1 | 9/2004 | Araki |
| 6,944,474 | B2 | 9/2005 | Rader et al. |

(Continued)

FOREIGN PATENT DOCUMENTS

| | | |
|---|---|---|
| WO | 2014/193264 A1 | 12/2014 |
| WO | 2016/153825 A1 | 9/2016 |

OTHER PUBLICATIONS

Bredikhin, WO 2014/193264, Dec. 4, 2014, machine translation.*

(Continued)

*Primary Examiner* — Brian Ensey
(74) *Attorney, Agent, or Firm* — Womble Bond Dickinson (US) LLP; Joseph Bach, Esq.

(57) ABSTRACT

This invention describes methods of Audio Signal Personalized Enhancement for optimal listening to music. A combination of hearing test, audio signal compensation, and signal processing algorithms are implemented jointly in an audio Device. An audio signal is processed and tuned within the entire range of audible frequencies to actively compensate for both the characteristics of the listening device, and the specific hearing characteristics of the listener, resulting in a much improved music listening experience. A randomized self-test algorithm is used to analyze user's hearing ability in each ear within a preselected dynamic volume range at multiple frequencies spanning the audible spectrum.

21 Claims, 4 Drawing Sheets

(56) References Cited

U.S. PATENT DOCUMENTS

| | | | |
|---|---|---|---|
| 7,328,151 B2 | 2/2008 | Muesch | |
| 7,529,545 B2 | 5/2009 | Rader et al. | |
| 8,112,166 B2 | 2/2012 | Pavlovic et al. | |
| 9,532,154 B2 * | 12/2016 | Bang ..................... | A61B 5/123 |
| 2010/0119093 A1 | 5/2010 | Uzuanis et al. | |
| 2014/0254828 A1 | 9/2014 | Ray et al. | |
| 2014/0309549 A1 | 10/2014 | Selig et al. | |
| 2014/0314261 A1 | 10/2014 | Selig et al. | |
| 2014/0334644 A1 | 11/2014 | Selig et al. | |

OTHER PUBLICATIONS

International Search Report and Written Opinion in PCT/US2016/022187 dated Jun. 7, 2016.

Yueh, Bevan et al., "Screening and Management of Adult Hearing Loss in Primary Care", Scientific Review, The Journal of the American Medical Association, Apr. 16, 2003; vol. 289, No. 15; pp. 1976-1985.

Shargorodsky, Josef et al., "Change in Prevalence of Hearing Loss in US Adolescents", The Journal of the American Medical Association, Aug. 18, 2010; vol. 304, No. 7; pp. 772-778.

* cited by examiner

SYSTEM AND METHOD FOR IMPROVED AUDIO PERCEPTION

RELATED APPLICATION

This Application claims priority benefit from U.S. Provisional Patent Application No. 62/177,631, filed Mar. 20, 2015, the disclosure of which is incorporated herein by reference in its entirety.

BACKGROUND

1. Field

The present invention is in the technical field of Audio Signal Processing and, more specifically, to processing of audio signals to compensate for hearing variations of users' hearing.

2. Related Arts

An audiogram is a graph that shows the audible threshold for standardized frequencies as measured by an audiometer. The Y axis represents intensity measured in decibels and the X axis represents frequency measured in Hertz. The threshold of hearing is plotted relative to a standardized curve that represents 'normal' hearing, in dB (HL).

Hearing thresholds of humans and other mammals can be found by using behavioural hearing tests or physiological tests. An audiogram can be obtained using a behavioural hearing test called Audiometry. For humans the test involves different tones being presented at a specific frequency (pitch) and intensity (loudness). When the person hears the sound they raise their hand or press a button so that the tester knows that they have heard it. The lowest intensity sound they can hear is recorded.

Ideally the audiogram would show a straight line, but in practice everyone is slightly different, and small variations are considered normal. Larger variations, especially below the norm, may indicate hearing impairment which occurs to some extent with increasing age, but may be exacerbated by prolonged exposure to fairly high noise levels such as by living close to an airport or busy road, work related exposure to high noise, or brief exposure to very high sound levels such as gunshot or music in either a loud band or clubs and pubs. Hearing impairment may also be the result of certain diseases such as CMV or Meniere's disease and these can be diagnosed from the shape of the audiogram.

Aside from hearing impairment, even the most expensive speakers or personal listening devices, such as, e.g., hi-fi stereo headphones with nearly perfect dynamic and spectral frequency characteristics, will produce very different results from one individual to another, depending on their respective hearing abilities. The existing amplifiers or media players are not equipped to provide a listening experience compensated for the listener's specific hearing limitations. The user can typically adjust only the low and high frequency signal levels of the playback device (i.e., bass and treble control) and, in more sophisticated players a simple equalizer can be used to reshape the audio signal according to the listener's personal taste and subjective "feeling". There are several key disadvantages to any of the above methods.

Figure 1:
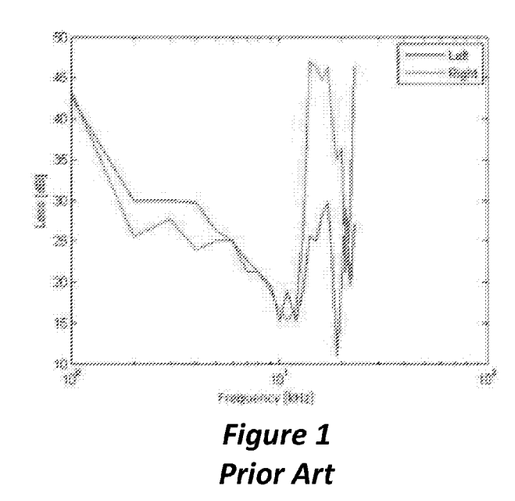
FIG. 1 is an example plot of left and right full spectrum hearing profile.

Generally, the user does not know how to tune each control, as the user does not know the details of his/her hearing characteristics. While hearing sensitivity frequently starts degrading only at high or low frequencies, notches (loss of sensitivity in a narrow spectral range) and un-equal hearing characteristic in both ears are quite common among all age groups. An example of such a hearing characteristic is illustrated in an audiogram in FIG. 1, showing the left and right full spectrum hearing profile. In the diagram of FIG. 1, the sensitivity loss in dB (Y axis) which is plotted as a function of test signal frequency in KHz (X axis) can be easily identified.

Additionally, the adjustment range of prior art equalizers in playback devices is very limited in terms of frequency range, number and width of adjustable bands, and volume levels. Similarly, prior art playback devices do not allow for a dedicated setup per each ear, except for the use of the balance function and a relative (left-right channel) adjustment of volume.

Whereas the commonly used sound equalizers can to a degree compensate for some of the hearing sensitivity loss, it is still true that listening to music from playback devices even through high quality headphones can be dissatisfying and frustrating for users with hearing limitations. To compensate for the reduced ability to hear instrumental and vocal sounds (frequently in a narrow spectral range or partially in one ear), many consumers listen to music at a greatly increased volume, inadvertently risking further hearing degradation. A personalized spectral compensation of the audio signal that counters the specific hearing limitations only within the affected frequency bands offers a much more effective and safer approach to dealing with a moderate hearing degradation and results in a greatly improved listening experience.

It has been well documented in various medical studies (e.g. "Screening and Management of Adult Hearing Loss in Primary Care", Scientific Review, The Journal of the American Medical Association, Bevan Yueh et al., 2003; 289(15): 1976-1985), that person's hearing ability degrades gradually with age. Notably, most people age 35 and up exhibit some degree of natural hearing degradation, which can be responsible for reduced enjoyment of music. Moreover, recent studies (e.g. The Journal of the American Medical Association, Vol. 304, No. 7, 2010) have shown that one in five teenagers in the United States suffers from hearing degradation believed to be caused by proliferation and improper use of personal playback devices. Individual's hearing ability may vary across many variables, including hearing thresholds and noise ambient, sensitivity to specific sounds, dynamic response to loud signals, physical nature of hearing impairment, and psycho-acoustical factors such as e.g. context of the sound. The hearing loss mechanism can be conductive (caused by problems in the outer or middle ear), sensorineural (caused by problems in the cochlea), or neural—caused by a problem in the auditory nerve or auditory pathways/cortex of the brain.

In many situations for hearing impaired an individually tailored hearing aid is frequently the best solution. The process of selecting the hearing aid entails detailed testing in an audiologist office using sophisticated equipment and highly trained personnel. In a typical audiogram the hearing sensitivity response is measured using limited four to eight basic frequency bands with the focus on understanding of human speech in noisy environments. Filtering out the noise from the background and/or selectively amplifying signal-of-interest is of primary importance to hearing aid design. Consequently, hearing aids are typically good at correcting a relatively narrow frequency range with focus on 3 KHz-4 KHz band corresponding to the human voice, while an average human auditory range extends from 20 Hz to beyond 16 kHz. Moreover, hearing aid devices are inherently different from playback devices because they are built for use in an open-air environment and can't be used to listen to music together with headphones or earphones.

The rise of the Internet has opened possibility for various on-line hearing tests and development of personalization techniques taking into account individuals hearing profiles. Number of testing regimes and methods have been offered in recent years, however, few were successful at providing an effective, automated sound personalization that could be practically implemented in common playback devices in everyday use. The various sound enhancement and compensation methods commonly used in today's playback devices include passive noise attenuation, selective amplification of the signal of interest, statistical signal filtering, automatic gain control (AGC), active noise cancelation, or any combination of the above.

In a recent patent (U.S. Pat. No. 8,112,166) by Pavlovic et al., the authors conclude that the efforts in the art have not succeeded in providing a system for effectively and rapidly generating individual's hearing profile, quote: "The most widespread employment of individual hearing profiles remains in the hearing aid field, where some degree of hearing impairment makes intervention a necessity."

In another patent example (U.S. Pat. Nos. 6,944,474 and 7,529,545) Rader et al., attempted methods of personalizing audio signals based on individual's hearing profile, personal preferences, and environmental noise factors. In this example a personal communication device such as e.g. smart phone comprising a control circuitry and logic, is used to apply multiband compression to the audio signals using the parameters derived from standard, age dependent, externally stored hearing profiles. In this approach, the signal effects are adjusted based among others on perceived sensitivity of the ears of the individual. However, the inventors don't teach the exact methods of measuring the hearing impairment nor do they explain how the elevated threshold of audibility of a tone due to impairment at a given frequency is used to modify the full frequency dynamic compression (FFDC) algorithm and the corresponding automatic gain control (AGC) proposed in the patent. The authors aspire to replicate the function of the healthy cochlea by compressing the sound such that the audio signal is no longer distorted in the auditory system. This approach has been proposed in monaural Bluetooth listening devices, which are not commonly used for listening to music.

In another set of patent publications (US 2014/0334644 A1, US 2014/0309549 A1 and US 2014/0314261 A1) Selig et al., describes several "Methods for Augmenting Hearing". In one variation, a mobile device is outputting a tone in its hearing test. Based on the user response to the tone, the method qualifies the signal as a particular audio type (based on pre-defined profiles), and process the audio signal based on that profile. A variation of this method selects a suitable profile based on the location of the audio device. Another variation tries to select from a pre-defined hearing models by outputting two tones to the user and recording the user's volume adjustment. These methods have a major limitation in the fact that they try to best match the user's hearing profile to a set of pre-defined and stored profile. While this method can provide audible results, it can't provide a perfect match to the user's hearing profile and deficiencies, and hence cannot truly compensate for all of the user's specific hearing deficiencies, nor to the dynamic and the frequency response of the playback devices used.

SUMMARY

The following summary of the disclosure is included in order to provide a basic understanding of some aspects and features of the invention. This summary is not an extensive overview of the invention and as such it is not intended to particularly identify key or critical elements of the invention or to delineate the scope of the invention. Its sole purpose is to present some concepts of the invention in a simplified form as a prelude to the more detailed description that is presented below.

Embodiments of the disclosed invention address the limitations of the prior art and enable an audio signal compensation for wide audiences with both common and custom hearing profiles.

According to disclosed embodiments, the individual profile and levels of hearing degradation are measured using an air-conduction test administered through the actual speakers, headphones or ear buds used for everyday listening to music. The test is simple, automated, and delivered by the playback device.

Embodiments of the invention propose specific personalization test method and, subsequently, signal processing methods for the enhancement of the audio signal based on listener's hearing sensitivity using the specific listening headset. The method can be implemented in consumer audio listening devices (playback device) including, but not limited to amplifiers, media players, cell phones, car and home audio systems, headphones, speaker systems, and musical instruments, using any audio source. The results of the test are used to generate a signal processing profile that is specific to the user-sounder pair. Thus, a particular user may have one profile for each sounder used by the user, e.g., one profile for personal headphone and one profile for the personal car.

Embodiments of the invention allow for a personalized correction and enhancement of the audio signal enabling the user of the device to have a listening experience similar to that of a young person with good hearing. This includes, in particular, equal hearing in both ears, compensation for partial hearing loss at low and high frequencies, compensation for narrow-band losses at middle frequencies ("notches") and fine control over the degree of said correction and thus the listening experience.

In the disclosed examples, the method is implemented by a two-step test and then use of the results of the tests for amplification correction. In these embodiments, the user's hearing is tested in two steps: an initial test is used to determine the initial dynamic volume range. The results of the initial tests are used to perform a second test that is used to determine sensitivity thresholds at individual frequencies. The results of the tests are stored as personal parameters for the individual tested. These parameters are then used as input parameters to the sound personalization and enhancement algorithms.

In some embodiments, the initial test is performed by playing a series of tones in ascending and/or descending frequencies within the audible spectrum. The user's responses to these tones are used to determine the initial dynamic volume range of the user's hearing. Also, the user's responses are used to set up the parameters of the second test. In disclosed embodiments, the second test is performed by playing individual, randomized, single frequency tones at volume levels controlled by a preprogrammed process. The user's responses to these single tones are used to determine sensitivity thresholds at individual frequencies. The softest volume level one can hear independently at each frequency and in each ear is defined as sensitivity threshold for that particular frequency for the respective ear. The hearing sensitivity thresholds and dynamic range values at each frequency are stored as personal parameters in the device's memory and are used as input parameters to the sound personalization and enhancement algorithms as part of the method.

In this aspect, the best results are achieved when the tests are performed using the same sounder that the particular user uses for listening to the music. In this description, the term "sounder" is used as a shorthand to refer to a particular amplification-driver combination, e.g., an iPhone® with Beats® Solo2 headphones, a laptop with Logitech®-Z313 2.1-Channel Speaker System, etc.

Embodiments of the invention provide an apparatus for sound reproduction, comprising a personalization module configured to receive user input and generate user hearing data, the personalization module may include a tone generator, a dynamic range calculation module, and a hearing data calculation module; a storage for storing the user hearing data; an equalizer design module may include an interpolator configured to interpolate the user hearing data to generate coefficient data and a transformer configured to transform the coefficient data into FIR coefficients; and an equalizer engine comprising a FIR filter and configured to receive sound signal input and apply the FIR filter using the FIR coefficients to the sound signal input to thereby generate equalized sound signal output.

In various embodiments, the tone generator may comprise one of a sine wave generator, a synthesizer, or a sampler. The tone generator may be configured to generate and output to the dynamic range calculation module a series of tones, each at a predetermined frequency and adjustable amplitude, and to generate and output to the hearing data calculation module single tones each at a predetermined frequency and adjustable amplitude. The tone generator is configured to adjust the amplitude of the series of tones and of the single tones according to input received from a user.

In some embodiments the apparatus may further comprise a compressor configured to apply a compression factor to thereby reduce the dynamic range of the equalized sound signal output. Also, the transformer may comprise an inverse Fast Fourier Transform.

BRIEF DESCRIPTION OF THE DRAWINGS

Other aspects and features of the invention would be apparent from the detailed description, which is made with reference to the following drawings. It should be appreciated that the detailed description and the drawings provides various non-limiting examples of various embodiments of the invention, which is defined by the appended claims.

The accompanying drawings, which are incorporated in and constitute a part of this specification, exemplify the embodiments of the present invention and, together with the description, serve to explain and illustrate principles of the invention. The drawings are intended to illustrate major features of the exemplary embodiments in a diagrammatic manner. The drawings are not intended to depict every feature of actual embodiments nor relative dimensions of the depicted elements, and are not drawn to scale.

DETAILED DESCRIPTION

Various features and aspects of the invention will now be described with reference to particular embodiments thereof. The disclosed embodiments may be implemented in hardware, software or a combination of hardware and software. The hardware may be a generic programmable or controllable hardware, or may be a specifically designed hardware. The disclosed embodiments may utilize standard speakers or headphones, energized by a standard amplifier. In the disclosed embodiments, personalized profiles are stored, such that if multiple users use the same audio equipment, the audio signal would be manipulated using the specific personalized profile of each user.

Disclosed embodiments of the invention include methods that are applicable to any audio signal format (analog and/or digital) and to any source or listening device, including for example: digital music players, smart phones, microphones, conventional digital or analog audio entertainment systems such as radios, TVs, CD players, and alike. The method may be implemented as a hardware device driven by a computer program, or by a computer program running in an existing device, e.g., a smartphone.

In some embodiments the hardware device can be a stand-alone dedicated device, an accessory to an existing device (e.g., add-on device), a hardware sub-system integrated into an existing hardware device (including, e.g., personal headphones, audio systems, personal/desktop speakers), etc.

The computer program may be implemented on different device types, including, but not limited to, cell phones, personal computers, laptops/notebook computers, e-readers, and home/car audio systems.

According to one embodiment of the present invention a self-test, consisting of the multi-band signal volume level selection and an automated threshold sensitivity detection algorithm, is implemented to generate user's hearing profile mapped in the entire audible frequency range up to 20 KHz. The self-test is implemented as an air-conduction test applied by the playback device. It is automated and designed to facilitate easy user interface and self-testing using the playback device. Another element of the invention comprises a set of signal compression and processing algorithms to compensate for the above measured hearing profile in combination with user defined preferences. Final element of the invention consists of a dedicated consumer device designed to implement the testing, compensation, and sound enhancement subject to the proposed method.

The specific implementation of the invention may include the following components:

Hearing Self-Test

This component of the invention consists of an automated hearing test delivered through a sounder and performed by the user at least once upon the first use of the device. A series of (preferably three) modified air conduction tests are performed individually for each ear. An individual hearing profile within the whole audible frequency range is recorded for each ear at 20-24 various frequencies in the range 20 Hz to 20,000 Hz. The hearing sensitivity threshold and the dynamic volume range at each test frequency are defined based on the user's feedback. Each ear's hearing profile is recorded and stored in the Device. A number of profiles for various users and/or various sounders can be stored.

Personalization

This component of the invention allows the playback device to create a personalized algorithm to tailor (personalize) the sound from the sounder in accordance with the listener's hearing profile characteristics determined and recorded during the hearing self-test. The individual setting for the user is typically performed once, upon first use of the particular sounder. However, it may be repeated as often as desired, and is always memorized when the playback device is left without power, even for a long time.

Compensation Calculation Algorithm

This component of the invention uses the personalization information for the user (personalized algorithm computed by the "Personalization" module above), and then computes the required Compensation Parameters for each ear used in the proposed signal compensation algorithm during playback.

Playback

After completion of the above three steps the sounder can be used for personalized listening to music. During the playback the device uses the Compensation Parameters calculated by the previous module to generate an efficient equalizer for each ear. The left/right music signals coming from the audio source are equalized separately by the generated equalizer, processed in real-time by the additional tailoring algorithm, and then passed to the corresponding listening device such as headphones, earphones, or speakers.

Acoustic Simulation

As noted before, existing playback devices do not provide compensation for specific hearing imperfections, which are matched and optimized for the individual listener. The following disclosure includes embodiments which provide the user with fast and accurate way to measure his/her hearing profile, to tune (via the Personalization module) the audio signal originating from the playback device according to his/her specific hearing characteristics, and provide the required signal compensation during playback using the device. The resulting listening experience is similar to the experience with a close to "perfect hearing".

Example 1

The following is an example for adjusting the equalization of audio player in a manner individualized for a user. The operations involved include performing a dynamic range calculation to determine the dynamic hearing range of the user for a plurality of predetermined frequencies; performing a hearing data calculation to determine an upper and a lower level for each of the plurality of predetermined frequencies for each ear of the user individually; using the output of the hearing data calculations to adjust an equalization of an audio player to obtain a user tailored equalization; and applying the user tailored equalization to an audio signal prior to playing the audio file to the user.

Figure 2:
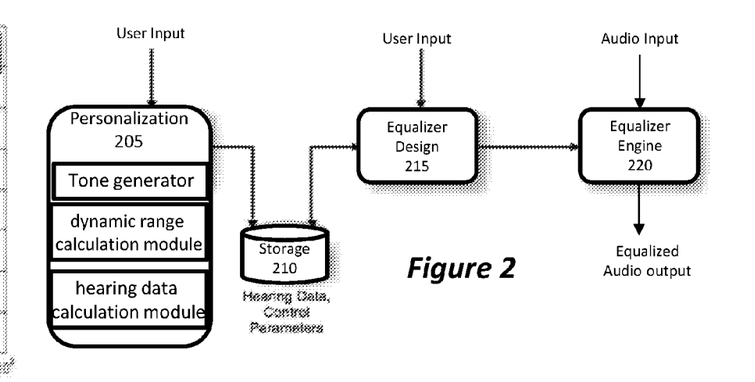
FIG. 2 is a block diagram illustrating the signal processing flow in an embodiment of the invention utilizing four modules.

FIG. 2 illustrates a block diagram of a signal flow for implementing this specific embodiment. In this embodiment, the audio signal personalization comprises several custom building blocks or modules. The modules may be implemented using Digital Signal Processing (DSP) and appropriate algorithms. One example of implementation of this embodiment is illustrated in FIG. 2, showing the signal path. As illustrated in FIG. 2, the processing chain comprises the following key algorithm/processing blocks:

1. Test-Personalization Module 205,
2. Equalizer Designer Module 215,
3. Equalizer Engine Module 220, and
4. Dedicated non-volatile memory module 210 for storing user's personalization data, or user-sounder data, and the corresponding equalizer control parameters.

In this example, the user input is used by the personalization module 205 to generate personalized hearing parameters that are individualized to the user and are specific and separate for each ear of the user. These hearing parameters may also be specific and individualized to the sounder used for the testing. To generate these personalized hearing parameters, the personalization module 205 may include a dynamic range calculation module and a hearing data calculation module. Also, a tone generator may be included to generate the tones used during the hearing tests. The tone generator may be a sampler, a synthesizer, or simply a sine-wave generator.

The personalized hearing parameters are stored in non-volatile storage memory 210. As will be discussed more fully below, in some embodiments the user has the option to tailor the design of the equalizer by, for example, controlling the effect of the equalization according to the stored parameters. This is referred to herein as compression factor. When this option is implemented, the user input is provided to the equalizer design 215 to apply a compression factor to the tailored equalization to thereby reduce the dynamic range of the tailored equalization.

Once the set-up of the equalizer engine is completed, the audio input is equalized by the equalizer engine, so as to provide an equalized audio output specifically tailored to the user-sounder pair.

Example 2

Figure 3:
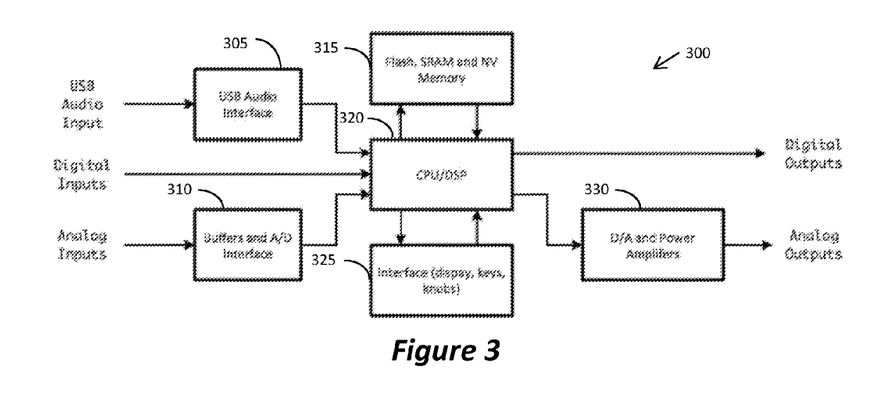
FIG. 3 is a block diagram illustrating the various modules utilized in an embodiment of the invention.

According to this embodiment, the modules of the invention are implemented in a specific hardware arrangement shown in FIG. 3. FIG. 3 is a hardware block diagram of the device 300 according to this specific example. In this example the device can accept various types of inputs:

Analog Inputs
Digital Inputs
USB Audio Input

The analog input to the device is passed to buffer amplifiers, followed by a A/D (Analog to Digital) converters indicated as 310. The outputs of the A/D converters are sent to the CPU/DSP 320 as a digital stream.

The device can also accept pure digital audio streams from various sources (e.g., S/PDIF connection, optical or coax), and audio steams over USB connection via USB audio interface 305. These streams pass through appropriate buffering/conditioning circuits to the CPU/DSP 320.

All interface components 325 (buttons, keypad, switches, indicators, and the display) are connected to proper interfaces. These, in turn, provide the appropriate connection to the CPU/DSP 320.

The CPU/DSP 320 is connected to three memory types, generally indicated as storage 315: Flash memory, EEPROM (referred as Non-Volatile Memory) and SRAM or DRAM. Some CPU/DSP devices provide on-chip Flash and SRAM memory, thus make it un-necessary to include external Flash/SRAM components. The Flash and EEPROM memory store all programs, parameters and data, which must be nonvolatile in the absence of power. The SRAM stores parameters and data while the device is operative.

The output of the CPU/DSP 320 can include several digital audio streams. These are fed to D/A (Digital to Analog) converters and from there to analog audio drivers, indicated collectively as 330. In one example, the D/A converters have the same number of bits and sampling frequency as the A/D converters.

The CPU/DSP 320 can also output dedicated digital audio streams, to allow connection to any audio playback device that can accept these types of streams.

The CPU/DSP 320 is responsible for running all the software that provides the functionality of the device. The CPU code is stored in an on-board/on-chip non-volatile memory (Flash).

In one example the operations to achieve aspects of the invention are embodied in a program that may be stored in memory 315 and, when executed causes the CPU/DSP 320 to perform the operation comprising: performing a dynamic range calculation to determine the dynamic hearing range of the user for a plurality of predetermined frequencies; performing a hearing data calculation to determine an upper and a lower level for each of the plurality of predetermined frequencies for each ear of the user individually; using the output of the hearing data calculations to adjust an equalization of an audio player to obtain a user tailored equalization; and applying the user tailored equalization to an audio signal prior to playing the audio file to the user.

Example 3

Figure 4:
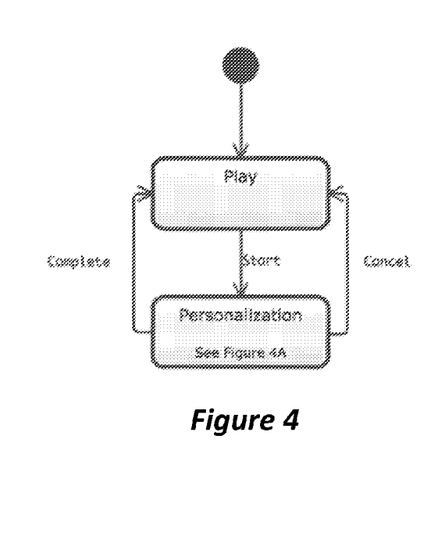
FIG. 4 is a device master state diagram as used in an embodiment of the invention.

This example illustrates a logical operation of an embodiment of the invention. FIG. 4 is a master State Diagram, explaining the logical operation of the disclosed embodiment. As can be seen from FIG. 4, the method has two logical operational states: Personalization and Play. In Personalization state, the device can be personalized to the user or to a user-sounder pair. The user may repeat the personalization operation as often as necessary by starting its process via the device user interface, e.g., interface 325 in FIG. 3. At the end of the personalization procedure, the device is "adapted" to the user or user-sounder pair such that the sound-processing algorithm is optimized for both ears over the whole frequency range. The Personalization parameters are saved to the Non-Volatile memory, e.g., memory 315 of FIG. 3. The user can restart Personalization in the middle of the play state as well. The user may also abort Personalization and switch to the Play state. When this happen, any measurements taken will not be saved. In Play state, the Device acts to compensate for the user's imperfect hearing according to the Personalization parameters computed during Personalization mode.

While in the Play state, the user can control the following parameters: Volume: this parameter controls the output volume of the Device; Balance: this parameter control the volume balance between the right and left audio channels; Bass, Treble: the parameters "Bass" and "Treble" provide additional boost/cut at low and high frequencies, similar to high-end room audio systems; Compression Factor: The parameter "Compression Factor" allows for partial compensation of the user's hearing instead of full compensation. This parameter helps the user to get used to the device during the initial period of usage by selecting the preferred degree of compensation; and Target Equalization Curve: this parameter defines the target frequency response curve that the device will generate, based on user's hearing data. Default Target Equalization Curve is flat, which represents a "perfect" hearing scenario, but other target curves can be used, to simulate certain loudspeakers' voicing, etc.

Example 4

The following example provides an embodiment of personalization algorithm, which measures and collects hearing parameters from the individual user. These parameters are in turn used to design equalizers matched to the user's hearing in both ears. Since many people suffer from unequal hearing in the two ears, it is essential to differentiate between the two ears in the equalization process; hence the need for collecting data from the two ears separately.

Humans' hearing spans a range of at most ten octaves, from 20 Hz to 20,000 Hz. However, accurate equalization in the first and last octave can be very difficult, because many (even most) people suffer from severe hearing loss at the corresponding frequencies. Thus, in some embodiments the testing is limited to frequencies from about 90 Hz to 5600 Hz. With respect to octave bands for the frequency range normally associated with hearing, the human ear is most sensitive at the $5^{th}$, $6^{th}$, $7^{th}$ and $8^{th}$ octave bands. Thus, in some other embodiments the testing is limited to frequencies from about 710 Hz to 11,200 Hz.

Moreover, full equalization (that is, full compensation of the loss) at those frequencies is not desired, because it is prone to signal distortion and unpleasant artificial effects. For these reasons, in one particular example the first and last octaves are excluded from the personalization procedure, such that the testing is limited to frequencies from about 90 Hz to 5600 Hz.

According to this specific embodiment, initial set of tones of discrete frequencies is selected. The discrete frequencies may be selected, e.g., on an approximate logarithmic scale, three frequencies per octave, for a total of 24 frequencies, in one specific example. The first and last octaves may be included or not. Alternatively, the frequencies may be selected only from the $5^{th}$-$8^{th}$ octaves. When the first and last octaves are used, the results may be used to fully or partially compensate for hearing loss. Also, in one specific example, 24 test tone frequencies are used for each ear, ranging from 50 Hz to 12 KHz.

Figure 4A:
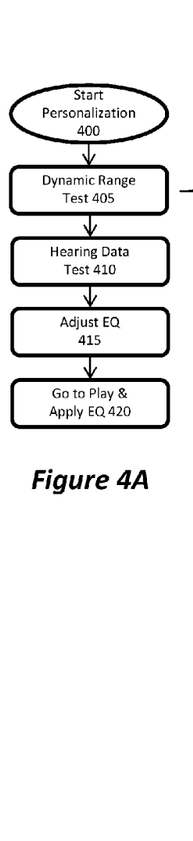
FIGS. 4A-4D are flow charts illustrating processes according to various embodiments of the invention.

The personalization test procedure, illustrated in FIG. 4A, is guided (by either voice or text instructions); therefore, the user is relieved from the need to read and memorize printed instructions.

The personalization procedure has two main steps:
Dynamic range calculation 405
Hearing Data calculation 410

When steps 405 and 410 are completed, the equalizer is adjusted at step 415 using the results of steps 405 and 410. The first step, 405, in the method of this embodiment is to calculate and adjust the user's hearing dynamic range, which consists of two separate volume levels:
An upper level, at which the user can hear all the tones (of the different frequencies) comfortably in each ear, and
A lower level, at which the user cannot hear any of the tones.

Figure 4B:
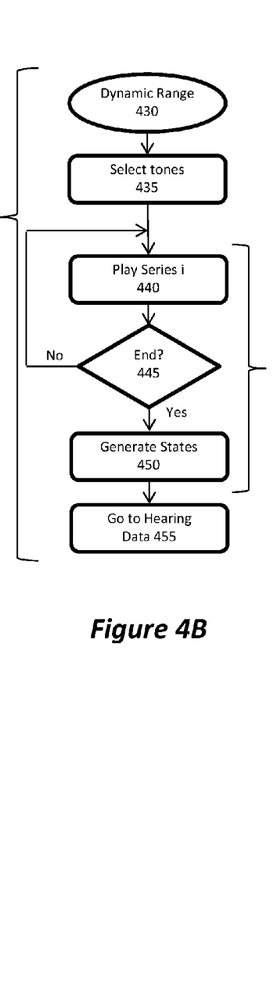

With reference to FIG. 4B, according to one embodiment, the first step, i.e., dynamic range calculation, is accomplished as follows. At step 435 a series of tones is selected. At step 440 the series is played in one ear (left or right) repeatedly, and the user is prompted to provide an input indicating the ability of the user to hear all of the tones in the series. This is repeated for the other ear. When this process ends at 445, the system generates a plurality of states at 450, using the data obtained from the testing procedure. The process then proceeds to perform the hearing data calculations at 455, using the states generated in step 450.

Figure 4C:
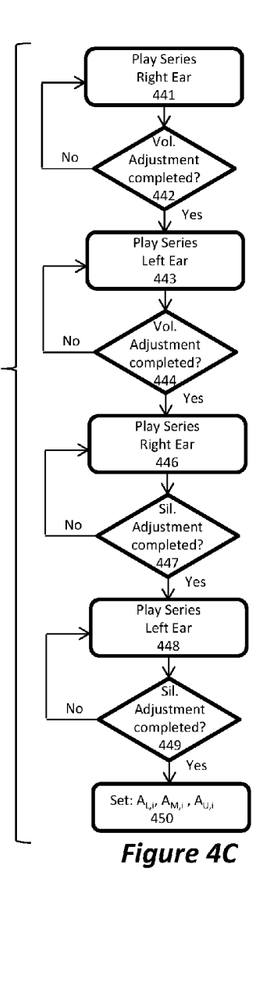

A more detailed example of the dynamic range procedure is provided in FIG. 4C. According to this embodiment, for each ear an upper level and a lower level are determined. In order to determine the upper level, a series of distinct tones is played to the user in each ear. The series is played sequentially, wherein at each play all of the tones are played one after the other in sequence. For example, if 24 frequencies were selected, then the program generates the 24 tones sequentially, one after another, e.g., in ascending order of frequency. The user is prompted to increase the volume, decrease the volume, or accept the volume, such that all of the tones are heard comfortably. This is done for each ear individually.

In order to determine the lower level, the same procedure is repeated, but this time the user is prompted to adjust the volume until nothing is heard. This concludes the initial test, according to which two volume levels have been established for each ear: upper volume level for each ear and lower volume level for each ear. Each volume level is applicable for the entire series, i.e., for all of the frequencies/tones in the series.

For example, in step 441 the series of tones is played in the right ear repeatedly as the user is adjusting the volume such that all the tones are heard comfortably. At step 442, once it is determined that the volume adjustment is completed, the process proceeds to step 443 wherein the series is played in the left ear. Again the user is asked to adjust the volume until all of the tones in the series are heard comfortably. When adjustment is completed at step 444, the process proceeds to step 446, wherein the series is again played in the right ear, but this time the user is asked to lower the volume until none of the tones in the series can be heard, i.e., until the user hears silence. This is repeated for the left ear at 448. When the process completes, the states are generated by setting tone/ear pairs and for each pair setting an upper level, a lower level and an intermediate level, which will be explained further below.

The second step in the method of this embodiment is the hearing data calculation. At the end of the dynamic range calculation procedure, the algorithm is equipped with four initial data values: an Upper Level and a Lower Level for each ear. In this particular example, all of the parameters are in dB. The algorithm now generates a set of 144 states: 72 states for each ear, and for each of the 24 tones there are 3 states. That is, for each ear and each frequency there are 3 states:

An Upper Level
A Lower Level
A Mid-Level.

The mid-level is taken as the mid-value of the upper and lower levels, in dB. Note, however, that other Intermediate Level may be used instead of a Mid-Level. For example, a multiplier k or a function f(j) may be used to determine the Intermediate-Level. Let us denote the three states of each ear/frequency pair by: $AL_{,i}$, $AM_{,i}$, $AU_{,i}$, where $1 \leq i \leq 48$.

Then, as we have said, all $AL_{,i}$ and $AU_{,i}$ are set according to the four values obtained as described above in the initial test, and $AM_{,i}$ is taken as 0.5(AL,i+AU,i) if the Mid-Level is used, as k(AL,i+AU,i) if the Intermediate-Level with multiplier is used (wherein 0<k<1), or some f(j)(AL,i+AU,i) if the Intermediate-Level is used with a function rather than a multiplier. At this point (from the results of the initial test) we are sure that the user can hear each frequency when it is sounded at level $AU_{,i}$, and cannot hear it when it is sounded at level AL,i.

According to this embodiment of the personalization algorithm the method proceeds to gradually decrease the distance between the upper level and the lower level of each ear/frequency pair, until this distance becomes smaller than a prescribed threshold. In this particular example, this is achieved as follows. An example is illustrated in the flow chart of FIG. 4D. At step 460 random number i is generated, in this example, between 1 and 48. At step 462 a short beep is sounded at ear/frequency pair determined by i, at level $AM_{,i}$. In some embodiments, the envelope of the beep waveform is smoothed at the edges in order to eliminate possible clicking sounds. The user is instructed to respond (e.g., press a button) if he/she hears the beep. The algorithm waits until the response is provided in step 464, or until a timed-out period has elapsed in step 466. In the latter case, the algorithm assumes that the beep was not heard.

Figure 4D:
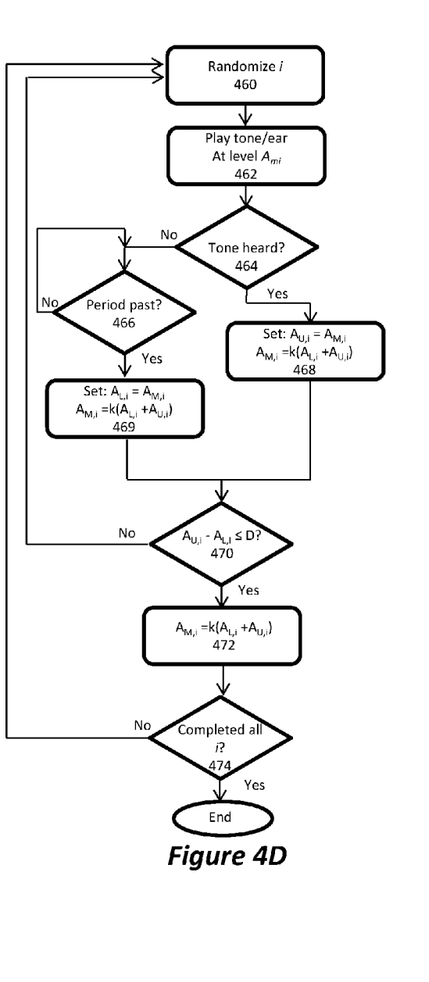

Now, state update is performed. Depending on the outcome, one of two choices is made: If the beep was heard, in step 468 the algorithm sets AU,i=AM,i and then updates AM,i as: AM,i=0.5(AL,i+AU,i), or AM,i=k(AL,i+AU,i) if the Intermediate-Level with multiplier is used. If the beep was not heard, at step 469 the algorithm sets AL,i=AM,i and then updates AM,i as: AM,i=0.5(AL,i+AU,i) or AM,i=k(AL,i+AU,i) if the Intermediate-Level with multiplier is used. In either case the distance between $AL_{,i}$ and AU,i is reduced, e.g., halved in the particular example where k=0.5. The algorithm thus continues, each time choosing i at random and reducing/halving the distance between the upper and lower levels of the corresponding ear/frequency pair. Randomization serves to eliminate the ear's "memory", which might bias the results. The randomization is applied both to which ear is tested and to which tone is tested.

When at step 470 a point is reached such that $A_{U,i} - A_{L,i} \leq D$, where D is a preset threshold value, the algorithm proceeds to step 472 wherein the algorithm may mark the $i^{th}$ ear/frequency pair as completed using the obtained AM,i. Alternatively, according to one embodiment, at step 470 when $A_{U,i} - A_{L,i} \leq D$, the process proceeds to step 472 and makes a final computation AM,i=0.5(AL,i+AU,i) or AM,i=k(AL,i+AU,i) if the Intermediate-Level with multiplier is used, and marks the $i^{th}$ ear/frequency pair as completed. The value $AM_{,i}$ is thus near the hearing threshold level of the user within +0.5D. This particular example uses D=2 dB, which makes the threshold level accurate to within ±1 dB.

Figure 5A:
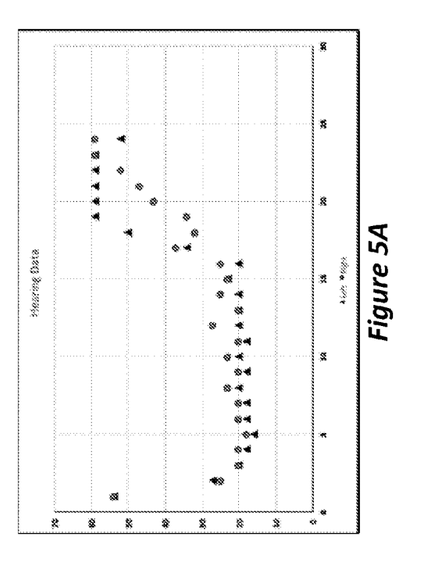
FIGS. 5A-5F are frequency response graphs illustrating the various steps when designing the equalizer based on user's hearing data.

After all ear/frequency pairs are marked as completed, the algorithm terminates, providing the 48 $AM_{,i}$ values as outputs. These values are referred to herein as the Hearing Data of the user. These values are stored in non-volatile memory, to make them available to the other algorithms' components. A graphic representation of the hearing data, representing each ear's hearing sensitivity per each test tone is shown in FIG. 5A.

Several users may use the same device (family or friends), in which case several hearing data sets are stored. Additionally, an individual user may use different earphones at different times. In this case the user is advised to perform personalization for each earphones pair separately and store the corresponding hearing data (as there are differences of frequency response and/or sensitivity between different earphone models).

The Equalizer Design Algorithm

The equalizer design algorithm operates behind the scenes and is not directly accessible to the user. This algorithm is entered in the following cases:

At the end of the personalization procedure.
When the user changes "Compression Factor".
When the user changes "Bass" or "Treble".
When the user changes the Target Equalization curve.

The equalizer design algorithm computes the equalizer's coefficients individually for each ear, based on the personalization data and optionally modified by the "compression factor", "Bass", and "Treble" data. The accuracy is determined to be compatible with the accuracy of the personalization data.

The equalizer design takes as inputs a set of 48 hearing data values, as described in the personalization algorithm and shown in FIG. 5A. These correspond to 24 values for the left ear and 24 values for the right ear, so we can focus our discussion on one channel only. We denote the set of hearing data by $A_i$, and recall that these are precisely the final values of $AM_i$ from the personalization algorithm.

In this particular embodiment the equalizer design adds two additional data values for each ear:

Data point at frequency 0, which is made equal to the value of the data point of lowest test tone. This extends the frequency response to 0 Hz.

Figure 5B:
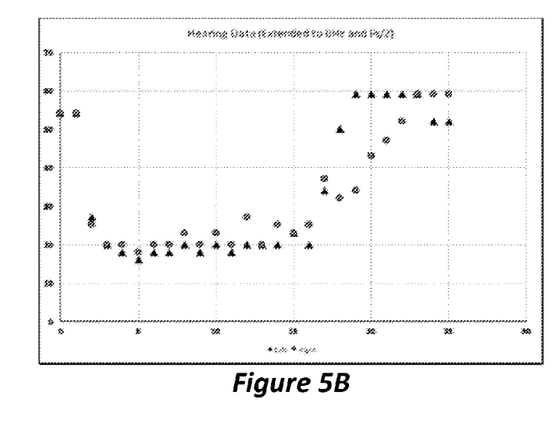

Data point at frequency Fs/2 (half the sample rate frequency), which is made equal to the value of the data point of the highest test tone. This extends the frequency response from our highest measurement frequency all the way to Fs/2. At this point we now have 26 measurements for each ear, as shown in FIG. 5B.

In addition to the hearing data, the algorithm is affected by several controls:
Compression Factor (optional)
Bass
Treble
Balance
Target Equalization Curve The value/state of these controls are set by the user and are stored in the non-volatile memory.

Common graphic equalizers use banks of recursive bandpass filters, where each such filter is tuned to a certain central frequency and a certain Q-factor. Equalizers of this type are not free of phase distortion; additionally, their amplitude-response characteristics are hard to control accurately.

The implementation adopted, instead, is a single high-order finite impulse response (FIR) filter equalizer. Such a filter can be made free of phase distortion (i.e., linear phase), and can have an accurate amplitude response. Additionally, FIR filters are known to have low sensitivity to computation noise, as well as efficient hardware architectures.

Figure 6:
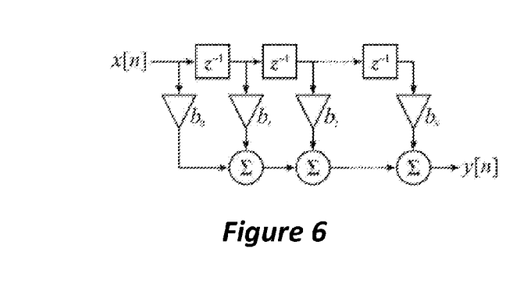
FIG. 6 is a block diagram illustrating a direct form discrete-time FIR filter of order N. The top part is an N-stage delay line with N+1 taps (coefficients) $b_0$ to $b_n$. $Z^{-1}$ is a delay stage of one sample time (1/Fs). X[n] denotes the input data samples, and y[n] is the filtered output.

The Equalizer Designer will compute the FIR coefficients based on the user's hearing data and the value of the controls. A graphic representation of a FIR filter is shown in FIG. 6, wherein x[n] represents the input signal (music to be played) and y[n] represents the output signal (the signal sent to the drivers—speakers or headphones). The FIR filter of this embodiment comprises N-stage delay line with N+1 taps (coefficients) $b_0$ to $b_n$, and $Z^{-1}$ is a delay stage of one sample time (1/Fs). The number of FIR coefficients should be selected based upon the required accuracy. The signals from all of the taps are summed to generate the output signal y[n]. In the next example we used n=512 FIR filter coefficients, and Sample Rate of 48 KHz.

Example 5

Figure 5C:
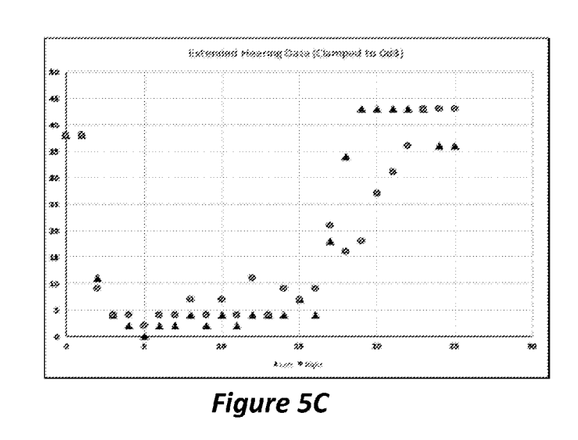

In the first step of the design, the Equalizer Designer "clamps" the extended user's Hearing Data to 0 dB value. This is done by finding the minimum value in the extended user's Hearing Data (both left and right ear data points, total 52 data points). After finding this value, we subtract it from each of the extended user's Hearing Data. After this operation, the lowest value in the user's extended Hearing Data will always be 0 dB, as can be seen in FIG. 5C.

Before describing the computation of the FIR coefficients, we must discuss the role of the optional control Compression Factor (CF).

The largest, $A_{iMax}$, and the smallest, $A_{iMin}$, of the 52 $A_i$ are identified. The difference, in dB, between the largest $A_{iMax}$ and the smallest $A_{iMin}$ of the 52 $A_i$ represents the dynamic range of the equalizer in the frequency domain. The dynamic range depends on the person's hearing and may reach several tens of dB for some hearing-impaired people. An equalizer having large dynamic range is prone to producing artifacts, such as whistles and echo-like sounds, which tend to occur when the input audio signal undergoes sudden changes. Additionally, people who have suffered from impaired hearing for many years are typically not used to having their hearing improved suddenly and may feel discomfort with the new sounds during the transition period.

For these reasons, the implementation included the optional CF control, whose aim is to reduce the dynamic range of the equalizer to a fraction of the full dynamic range provided by the hearing data.

According to one example, the CF takes a pre-set discrete values, e.g., 32 discrete values from 0 to 31, as controlled by the user. Its function is to modify each of the hearing data according to the formula:

$$A_{icf} = A_{min} + (Ai - A_{min})CF/32$$

Wherein $A_{icf}$ is the hearing data value after the application of the compression factor. We observe the following:
If CF=0, then $A_{icf} = A_{min}$, meaning that the equalizer is flat.
If CF=32, then there is no change in $A_{icf}$, meaning equalization at the full dynamic range.
For intermediate values of CF, the dynamic range changes from A max–$A_{min}$ to (A max–Amin) CF/32, so it becomes a fraction of the original dynamic range.

Figure 5D:
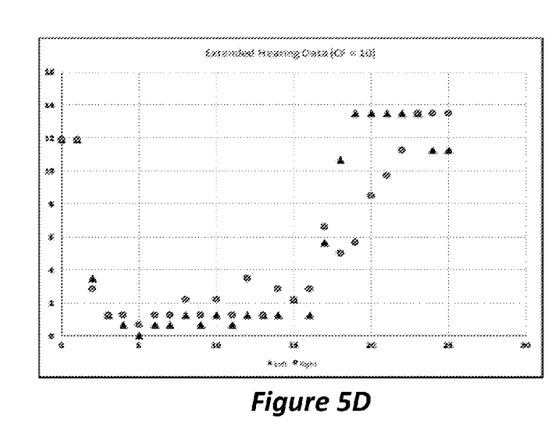

We have found that CF≈10 is a comfortable value for many beginning users, at the early period of adaptation. Later, when the user gets better used to the device, he or she may choose higher CF values. Values of CF near the maximum are likely to be better suited to users having only mild impairments. FIG. 5D shows the user's Extended Hearing Data after using CF=10. As can be seen, the plot of FIG. 5D is the same shape of FIG. 5C, except that the amplitude on the y-axis is reduced.

After the hearing data are corrected by the compression factor, the amplitude response is computed over the entire frequency range by the use of interpolation. This step uses the user's Extended Hearing Data (26 point for each year) and calculates additional data point for a total of N data values per each ear, wherein N is the number of coefficients of the FIR. This is required since we need to design an FIR of length 512 in this example, so the 26 points are extrapolated to generate 512 data values. The interpolation process creates a data set of 512 values per each ear, where each data set corresponds to the user's hearing sensitivity at frequency $$F[n] = n*Fs/512 \text{ (for } n=0,255)$$

Figure 5E:
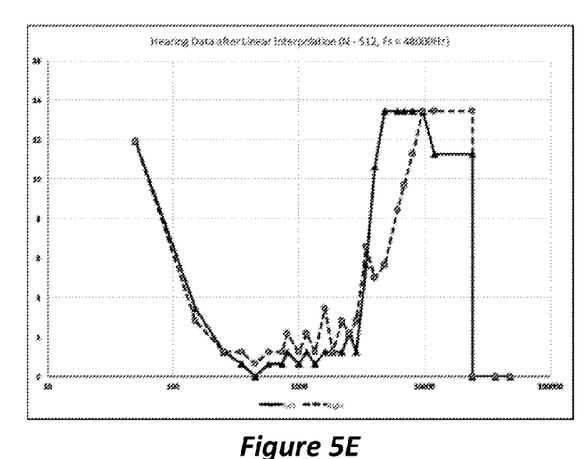

Note that for frequency equal or larger than Fs/2, we set the data point values to 0 (as required per Nyquist Law to prevent aliasing). This is illustrated in FIG. 5E.

The next step is the Target Equalization Curve (if needed). Up until this point, we were designing the equalizer to generate a flat frequency response result. Since we are operating in the frequency domain using the interpolated data set obtained in previous step, we can now create any required Equalization curve by manipulating specific data points. For example, if we want to increase the gain at frequency Fi by XdB, we add that extra gain to the value already at the data set:

$$\text{Amp Response}[Fi] += X$$

The next step is to add Bass (BA) and Treble (TR) controls. We now benefit from an additional advantage of the FIR approach, namely: the Bass and Treble can be easily included in the overall frequency response, and there is no need for additional Bass and Treble filters. The shapes of the two controls are preset and the control values are made to vary from −12 dB to +12 dB, in steps of 1 dB.

The last control to be added is the Balance (BA). This is simply included by adding half the balance value (in dB) to the right-channel equalizer and subtracting half the value from the left-channel equalizer.

Figure 5F:
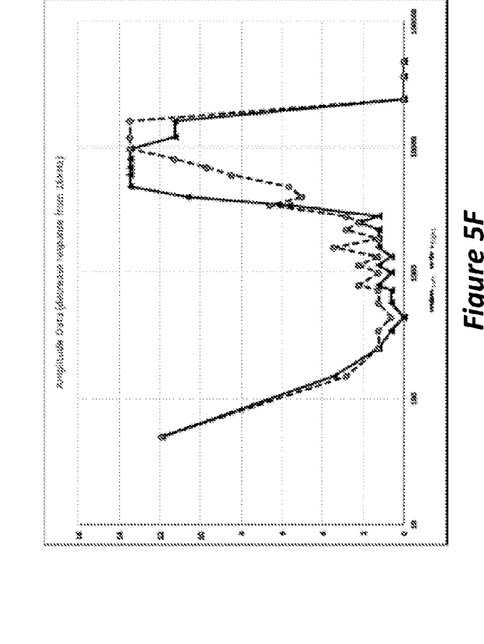

Before we design the equalizer, we may optionally decrease the target frequency response, e.g., linearly, down from 16000 Hz to Fs/2 (24000 Hz in our example). This is done to ease the FIR design process. This is shown in FIG. 5F.

At this point in the algorithm, the full amplitude response of each channel is available, at frequency resolution determined by the FIR length (512, for this example). In order to compute the required FIR coefficients$_{b0..511}$ we will use the Inverse Fast Fourier Transform (Inverse FFT). For the input of the Inverse FFT, we will use the phase as zero, and the data sets calculated in previous steps and the Amplitude Response (Real part). We create a symmetric FIR, which becomes linear-phase in causal implementation. A mild window (e.g., Hann function) is applied, to further smooth out the frequency response. At the end of this step, we have two sets of 512 FIR coefficients (one set for each ear), which can be used with an FIR filter implemented per FIG. 6.

The remaining step of the equalizer design algorithm is not directly related to the frequency response, but is aimed at initial setting of the volume control. The output energy of the equalized signal depends on both the input signal spectrum and the equalizer's frequency response. Whereas the latter is known, the former is hard to predict and varies with the music. We therefore used a "typical" music spectrum, whose energy is approximately equal at low and medium frequencies, and decreases at 40 dB/decade from a preset frequency upwards. The sum (in dB) of the input signal spectrum and the equalizer response gives the output signal spectrum, from which the energy can be easily calculated. The initial volume control then varies with the negative of the calculated energy, thereby making the perceived signal level approximately constant (means, the perceived volume level heard by the user will be the same whether the equalizer is engaged or not). Of course, the user can always adjust the volume control manually to a desired level.

Note that the user can change the values of the Compression Factor, Bass, and Treble controls and Target Curve selection at runtime. Any such change will trigger an automatic redesign of the Equalizer (e.g. the FIR filter coefficients), as described above, and will feed it to the Equalizer Engine. The user will be able to notice immediately the effect of any control change.

In one embodiment, the Equalizer Engine is implemented as a Symmetric FIR filter, per each ear, using the filter coefficients calculated in the previous steps.

If the target architecture does not support an efficient implementation of a Symmetric FIR, a standard FIR filter implementation can be used instead (by duplicating the calculated coefficients).

As can be understood from the above description and the corresponding Figures, embodiments of the invention enhance enjoyment of music, by generating an equalizer that is personalized to the specific user and the specific sounder used by the user. Embodiments of the invention may be implemented in hardware, in software, or in a combination of hardware and software. For example, an embodiment of the invention may be implemented in a non-transitory computer-readable medium comprising instructions stored thereon, that when executed on a processor, perform the steps of: performing a dynamic range calculation to determine the dynamic hearing range of the user for a plurality of predetermined frequencies; performing a hearing data calculation to determine an upper and a lower level for each of the plurality of predetermined frequencies for each ear of the user individually; using the output of the hearing data calculations to adjust an equalization of an audio player to obtain a user tailored equalization; and applying the user tailored equalization to an audio signal prior to playing the audio file to the user.

In some embodiments, the hearing data calculation generates N number of personalized hearing data, and further comprising a step of converting the personalized hearing data to equalization coefficient. The step of converting the personalized hearing data may include a step of extrapolating the N personalized hearing data into M extrapolated hearing data, and transforming the M extrapolated hearing data into M equalizer coefficients, wherein the M equalizer coefficients may be M coefficients of a FIR filter. The step of transforming the M extrapolated hearing data may be performed by applying an inverse Fast Fourier Transform to the M extrapolated hearing data. The embodiment may further include a step of applying a compression factor to thereby reduce the dynamic range of the tailored equalization.

While certain features of the invention have been illustrated and described herein, many modifications, substitutions, changes, and equivalents may occur to those skilled in the art. It is, therefore, to be understood that the appended claims are intended to cover all such modifications and changes as fall within the true spirit of the invention.

The invention claimed is:

1. A computer-implemented method for adjusting equalization of audio player individualized for a user, comprising:
   performing a dynamic range calculation to determine the dynamic hearing range of the user for a plurality of predetermined frequencies;
   performing a hearing data calculation to determine an upper and a lower level for each of the plurality of predetermined frequencies for each ear of the user individually;
   using the output of the hearing data calculations to adjust an equalization of an audio player to obtain a user tailored equalization;
   applying the user tailored equalization to an audio signal prior to playing the audio file to the user.

2. The method of claim 1, further comprising applying a compression factor to the tailored equalization to thereby reduce the dynamic range of the tailored equalization.

3. The method of claim 1, wherein performing a dynamic range calculation comprises obtaining a user input indicative of a volume level at which the plurality of predetermined frequencies can be heard and a level at which plurality of predetermined frequencies can no longer be heard by the user, for each ear independently.

4. The method of claim 3, wherein prior to obtaining the user's input, the plurality of predetermined frequencies are sounded as a series of tones in the user's ears.

5. The method of claim 4, wherein the series of tones exclude frequencies from first and last octaves audible to the user.

6. The method of claim 1, wherein performing a hearing data calculation comprises, for each of the plurality of predetermined frequencies determining an initial max level and an initial min level, and using a user's input to minimize the spread between each max level and its corresponding min level for each of the plurality of predetermined frequencies.

7. The method of claim 6, wherein when a minimized spread between a max level and its corresponding min level of one of the plurality of predetermined frequencies reaches a preset threshold, designating a hearing threshold level for that one of the plurality of predetermined frequencies.

8. The method of claim 7, wherein the hearing threshold level is calculated as the midpoint of the minimized spread between a max level and its corresponding min level.

9. The method of claim 7, further comprising applying a compression factor to the tailored equalization, wherein the compression factor is calculated as the spread between a highest one of the max level and the lowest one of the min level times a multiplier of between zero and one.

10. The method of claim 1, wherein adjusting an equalization of an audio player comprises modifying coefficients of a finite impulse response filter using the hearing data calculation.

11. The method of claim 1, wherein applying the user tailored equalization to an audio signal comprises applying separate equalization to left ear channel and to right ear channel.

12. A method for adjusting equalization of audio player individualized for a user, comprising:
    generating a series of a plurality of tones of different frequencies;
    performing the following operations at least once:
    sounding the series in one ear of the user and requesting an input from the user indicating whether all of the plurality of the tones were heard; and,
    playing the series in second ear of the user and requesting an input from the user indicating whether all of the plurality of the tones were heard;
    thereafter performing the operations:
    generating a set of multiple states, each state comprising one tone of the plurality of tones and having an assignment to left or right ear, having an assigned upper level, having an assigned lower level, and having an intermediate-level;
    sounding each of the states to the user and updating the states according to the user input to generate updated states; and,
    using the updates states to adjust the equalization.

13. The method of claim 12, wherein requesting an input from the user indicating whether all of the plurality of the tones were heard comprises at one stage requesting the user to adjust the volume until the series is heard comfortably and at a second stage requesting the user to adjust the volume until the series cannot be heard.

14. The method of claim 13, wherein the assigned upper level corresponds to the volume when the series is heard comfortably and the assigned lower level corresponds to the volume wherein the series cannot be heard.

15. The method of claim 14, wherein updating the states comprises minimizing a spread between the upper level and the lower level for each of the states.

16. The method of claim 15, wherein minimizing the spread comprises reducing the spread until the spread reaches a preset threshold.

17. The method of claim 16, further comprising setting a threshold level when a spread reaches a preset threshold.

18. The method of claim 12, wherein the step of sounding each of the states to the user and updating the states according to the user input to generate updated states comprises:
    performing the following operations a plurality of time:
    randomly selecting one of the state;
    sounding in one of the user's ears the tone corresponding to the state at an intermediate level that is between the assigned upper level and the assigned lower level;
    requesting the user to indicate whether the tone was heard and:
        if the tone was heard, setting the upper level to equal the intermediate level to thereby generate a revised upper level, and setting a revised intermediate level;
        if the tone was not heard, setting the lower level to equal the intermediate level to thereby generate a revised lower level, and setting a revised intermediate level;
        determining whether the spread between the revised upper level and the revised lower level reaches a preset threshold and, if so, setting the revised intermediate level as a hearing data for the selected state.

19. The method of claim 18, wherein using the updates states to adjust the equalization comprises applying the hearing data to a coefficients of a finite impulse response filter.

20. The method of claim 19, further comprising applying a compression factor to the coefficients of a finite impulse response filter to thereby reduce the dynamic range of the equalization.

21. The method of claim 19, wherein the compression factor is set by:
    determining a max upper level having the highest level of all the states;
    determining a min lower level having the lowest level of all the states;
    applying a fractional multiplier to the spread of the max upper level and the min lower level.

* * * * *